(12) United States Patent  (10) Patent No.: US 8,437,835 B2
Nemoto  (45) Date of Patent: May 7, 2013

(54) LIQUID INJECTOR DISPLAYING INPUT INJECTION CONDITION AS IMAGE

(75) Inventor: Shigeru Nemoto, Tokyo (JP)

(73) Assignee: Nemoto Kyorindo Co., Ltd, Tokyo (JP)

(*) Notice: Subject to any disclaimer, the term of this patent is extended or adjusted under 35 U.S.C. 154(b) by 1887 days.

(21) Appl. No.: 10/565,085

(22) PCT Filed: Jul. 7, 2004

(86) PCT No.: PCT/JP2004/009637
§ 371 (c)(1),
(2), (4) Date: Jan. 17, 2006

(87) PCT Pub. No.: WO2005/007200
PCT Pub. Date: Jan. 27, 2005

(65) Prior Publication Data
US 2006/0184122 A1 Aug. 17, 2006

(30) Foreign Application Priority Data
Jul. 18, 2003 (JP) ................... 2003-276639

(51) Int. Cl.
A61M 5/142 (2006.01)
A61B 6/00 (2006.01)

(52) U.S. Cl.
USPC ............................ 600/432; 600/431; 604/131

(58) Field of Classification Search ............... 600/432, 600/431; 604/131
See application file for complete search history.

(56) References Cited

U.S. PATENT DOCUMENTS

| 4,785,799 A | 11/1988 | Schoon et al. |
| 4,925,444 A | 5/1990 | Orkin et al. |
| 5,088,981 A | 2/1992 | Howson et al. |
| 5,530,796 A * | 6/1996 | Wang ......................... 715/762 |

(Continued)

FOREIGN PATENT DOCUMENTS

| EP | 0985421 A2 | 3/2000 |
| GB | 2 312 055 A | 10/1997 |

(Continued)

OTHER PUBLICATIONS

First Office Action for Chinese Patent Application No. 200480019797.4 dated Jun. 27, 2008 by State Intellectual Property Office of People's Republic of China.

(Continued)

*Primary Examiner* — Tse Chen
*Assistant Examiner* — Bradley Impink
(74) *Attorney, Agent, or Firm* — Knobbe, Martens, Olson & Bear, LLP

(57) ABSTRACT

The preset invention provides a liquid injector in which, when an injection time period and an injection rate are entered as an injection condition, a condition image having a horizontal width corresponding to the injection time period and including the injection rate as text data is displayed in a condition screen with its vertical axis representing the injection rate and its horizontal axis representing the injection time period at a vertical position in association with the injection rate and a horizontal position in association with the injection time period. The operator easily understands instinctively the injection condition from the horizontal width and the position of the condition image, and since the condition image includes the injection rate as text data, the operator can check quickly the numerical values. Thus, the liquid injector can be provided which allows simple entry and review of the injection condition.

11 Claims, 13 Drawing Sheets

U.S. PATENT DOCUMENTS

| | | | |
|---|---|---|---|
| 5,662,612 | A | 9/1997 | Niehoff |
| 5,823,363 | A * | 10/1998 | Cassel .......................... 211/60.1 |
| 6,337,992 | B1 | 1/2002 | Gelman |
| 2002/0007116 | A1 * | 1/2002 | Zatezalo et al. .............. 600/432 |
| 2004/0057061 | A1 * | 3/2004 | Bochkarev .................... 358/1.9 |

FOREIGN PATENT DOCUMENTS

| | | |
|---|---|---|
| JP | 55-119711 | 9/1980 |
| JP | 55-158054 | 12/1980 |
| JP | 62-34571 | 2/1987 |
| JP | 01-265973 | 10/1989 |
| JP | 2002-011096 | 1/2002 |
| JP | 2002-102343 | 4/2002 |
| JP | 2003-505211 | 2/2003 |
| JP | 2003-290343 | 10/2003 |
| JP | 2004-298549 | 10/2004 |
| WO | WO 96/32975 | 10/1996 |
| WO | WO 00/61216 | 10/2000 |
| WO | WO 01/08730 A1 | 2/2001 |

OTHER PUBLICATIONS

Supplementary Partial European Search Report dated May 7, 2007.
Notice of Reason(s) for Rejection for Japanese patent application No. 2005-511814 dated Apr. 7, 2010 by Japanese Patent Office.
International Preliminary Report on Patentability for International patent application No. PCT/JP2004/009637 dated May 22, 2006 by the International Bureau of WIPO.

* cited by examiner

LIQUID INJECTOR DISPLAYING INPUT INJECTION CONDITION AS IMAGE

TECHNICAL FIELD

The present invention relates to a liquid injector for injecting a liquid into a patient, and more particularly to a liquid injector for injecting a liquid, such as a contrast media, into a patient who is to be imaged by an imaging diagnostic apparatus such as a CT (Computed Tomography) apparatus, an MRI (Magnetic Resonance Imaging) apparatus, a PET (Positron Emission Tomography) apparatus, or the like.

BACKGROUND ART

Presently available imaging diagnostic apparatus for capturing fluoroscopic images of patients include CT scanners, MRI apparatus, PET apparatus, ultrasonic diagnostic apparatus, CT angiography apparatus, MR angiography apparatus, and ultrasonograph. When such an imaging diagnostic apparatus is used to capture a fluoroscopic image of a patient, it is occasionally practiced to inject a liquid such as a contrast media or a physiological saline into the patient. A liquid injector for automatically injecting a liquid into a patient has been commercially available.

Such a liquid injector has a drive motor and a slider mechanism and the like, and employs a liquid syringe that is removably mounted. The liquid syringe comprises a cylinder member and a piston member slidably inserted in the cylinder member. The cylinder member is filled with a liquid such as a contrast media or a physiological saline to be injected into the patient.

The liquid syringe is connected to the patient by an extension tube and set on an injection performing means. The injection performing means individually holds the piston member and the cylinder member and moves them relatively to each other for injecting a liquid, typically a contrast media, from the liquid syringe into the patient.

The operator determines the rate at which the contrast media is to be injected and the total quantity of the contrast media to be injected, in view of various conditions, and then enters numerical data representing the rate and total quantity into the liquid injector. Based on the entered numerical data, the liquid injector injects the contrast media into the patient at the rate and in the quantity represented by the entered numerical data. The injected contrast media changes the image contrast of the patient, allowing the imaging diagnostic apparatus to capture a good fluoroscopic image of the patient.

Some liquid injectors are capable of injecting a physiological saline as well as a contrast media into the patient. For operating such a liquid injector, the operator enters, if desired, an instruction to inject the physiological saline following the completion of the injection of the contrast media, together with data representing the rate at which the physiological saline is to be injected and the total quantity of the physiological saline to be injected, into the liquid injector.

Based on the entered data, the liquid injector first injects the contrast media and then automatically injects the physiological saline after the contrast media has been injected. The subsequently injected physiological saline pushes the previously injected contrast media, reducing the consumption of the contrast media, and also reduces artifacts in the captured image.

Liquid injectors of the type described above have been devised and applied for patent by the applicant of the present application (see, for example, patent documents 1, 2 below).

The above liquid injector is capable of injecting a contrast media into the patient in order to change the image contrast of the patient to a state which allows the imaging diagnostic apparatus to capture a good fluoroscopic image of the patient.

When a contrast media for CT was actually injected into a patient by the liquid injector and a time-dependent change in the CT value, which represents the image contrast, was measured, it was found that even if the contrast media was injected at a constant rate, the CT value was not constant, but rose nonlinearly and then fell, and remained at an optimum level for a very short period of time.

Therefore, the conventional liquid injector which injects a contrast media at a constant rate that is represented by entered numerical data fails to provide optimum-imaging conditions in an imaging diagnostic apparatus combined therewith. For solving the above problem, it is necessary to change, with time, the rate at which the contrast media is injected. For example, it is known in the art to divide one cycle of liquid injection into a plurality of phases and set numerical values of a liquid injection rate and a liquid injection time for each of the phases.

However, in the liquid injector described above, when the operator enters numerical data representing injection condition such as the injection rate with a numeric keypad, the entered numerical data is only displayed as text data, and thus it is difficult for the operator to understand intuitively the injection condition from that displayed data. Therefore, the operation is complicated and is not easy for an unskilled operator, and entry of inappropriate numerical values cannot be prevented.

To solve the abovementioned problem, the present applicant has devised a liquid injector in which an operator enters injection conditions including a relationship between an injection time period and an injection rate to a touch panel and the entered injection condition is displayed on the touch panel to control the operation of liquid injection in real time in accordance with the injection condition, and has applied it as Japanese patent application No. 2002-099928 and Japanese patent application No. 2003-098057.

However, such detailed entries and control may not be required in the actual medical environment, and simpler input actions and displays may be desired. In addition, the operator can easily understand instinctively the injection condition as described above, but the numerical values of the injection condition is difficult to review quickly.

LIST OF REFERENCES

Patent document 1: Japanese laid-open patent publication. No. 2002-11096;
Patent document 2: Japanese laid-open patent publication No. 2002-102343.

DISCLOSURE OF INVENTION

The present invention has been made in view of the abovementioned problems, and it is an object of the present invention to provide a liquid injector which allows simple and easy input actions of an injection condition, instinctive understanding of the injection condition, and quick check of the numerical values.

According to a first aspect and a second aspect of the present invention, the liquid injector injects at least one liquid to a patient and includes a screen displaying means, a condition entering means, an image producing means, an image displaying means, a state detecting means, an injection control means, and an injection performing means.

In the liquid injector according to the first aspect of the present invention, the screen displaying means displays a condition screen with its vertical axis representing an injection rate of the liquid and its horizontal axis representing an injection time period of the liquid. The condition entering means accepts an input action of at least one injection condition including an injection rate of the liquid relative to the injection time period. The condition storing means stores the entered injection condition. The image producing means produces a condition image having a horizontal width corresponding to the injection time period and including at least the injection rate as text data for each of the stored injection conditions. The image displaying means displays the at least one produced condition image in the condition screen at a vertical position in association with the injection rate and a horizontal position in association with the injection time period. The state detecting means measures at least the elapsed time from the start of the injection of the liquid. The injection control means controls the operation of the injection performing means in real time in accordance with the measured elapsed time and the stored injection condition. The injection performing means performs the injection of the liquid.

Thus, in the liquid injector of the present invention, when the operator enters the injection time period and the injection rate as the injection condition, the condition image having the horizontal width corresponding to the injection time period and including the injection rate as text data is displayed in the condition screen with its vertical axis representing the injection rate and its horizontal axis representing the injection time period at the vertical position in association with the injection rate and the horizontal position in association with the injection time period.

In the liquid injector of the first aspect of the present invention, it is. only necessary for the operator to enter the injection time period and the injection rate as the injection condition, so that the input action is simple and easy. Since the condition image having the horizontal width corresponding to the injection time period and including the injection rate as text data is displayed in the condition screen with its vertical axis representing the injection rate and its horizontal axis representing the injection time period at the vertical position in association with the injection rate and the horizontal position in association with the injection time period, the operator easily understands instinctively the injection condition from the horizontal width and the position of the condition image. In addition, the injection rate is included as text data in the condition image, so that the operator can quickly check the numerical values thereof.

In the liquid injector according to the second aspect of the present invention, the screen displaying means displays a condition screen with its vertical axis representing an injection rate of the liquid and its horizontal axis representing an injection quantity of the liquid. The condition entering means accepts an input action of at least one injection condition including an injection rate of the liquid relative to the injection quantity. The image producing means produces a condition image having a horizontal width corresponding to the injection quantity and including at least the injection rate as text data for each of the stored injection conditions. The image displaying means displays the at least one produced condition image in the condition screen at a vertical position in association with the injection rate and a horizontal position in association with the injection quantity. The state detecting means detects at least the injection quantity from the start of the injection of the liquid. The injection control means controls the operation of the injection performing means in real time in accordance with the detected injection quantity and the stored injection condition.

Thus, in the liquid injector of the present invention, when the operator enters the injection quantity and the injection rate as the injection condition, the condition image having the horizontal width corresponding to the injection quantity and including the injection rate as text data is displayed in the condition screen with its vertical axis representing the injection rate and its horizontal axis representing the injection quantity at the vertical position in association with the injection rate and the horizontal position in association with the injection quantity.

In the liquid injector of the second aspect of the present invention, it is only necessary for the operator to enter the injection quantity and the injection rate as the injection condition, so that the input action is simple and easy. Since the condition image having the horizontal width corresponding to the injection quantity and including the injection rate as text data is displayed in the condition screen with its vertical axis representing the injection rate and its horizontal axis representing the injection quantity at the vertical position in association with the injection rate and the horizontal position in association with the injection quantity, the operator easily understands instinctively the injection condition from the horizontal width and the position of the condition image. In addition, the injection rate is included as text data in the condition image, so that the operator can quickly check the numerical values thereof.

The various means referred to in the present invention may be arranged to perform their stated functions, and may be implemented by dedicated pieces of hardware for performing the functions, data processing apparatus for performing the functions according to computer programs, functions achieved in data processing apparatus according to computer programs, or combinations thereof.

The various means referred to in the present invention are not required to be individually independent entities, and may be arranged such that a plurality of means may be constructed as a single apparatus, a certain means may be part of another means, or part of a certain means and part of another means overlap each other.

Certain terms with respect to forward, rearward, upward, downward, leftward, and rightward directions which will be referred to in the description are used for convenience only to simplify the illustration of relative positional relationships of various parts, and should not be interpreted as being limited to directions that are involved when the liquid injection system is manufactured and used.

BEST MODE FOR CARRYING OUT THE INVENTION

[Configuration of the Embodiment]

Explanation is presented below regarding an embodiment of the present invention referring to drawings. The liquid injection system 1000A of an embodiment according to the present invention, comprises liquid injector 100, liquid syringe 200 and MRI apparatus 300, which is a diagnostic imaging apparatus, as shown in FIG. 1 to FIG. 4. The system is intended for injecting a contrast media or the like as a liquid to a patient (not shown) as will be described in detail later.

Figure 3:
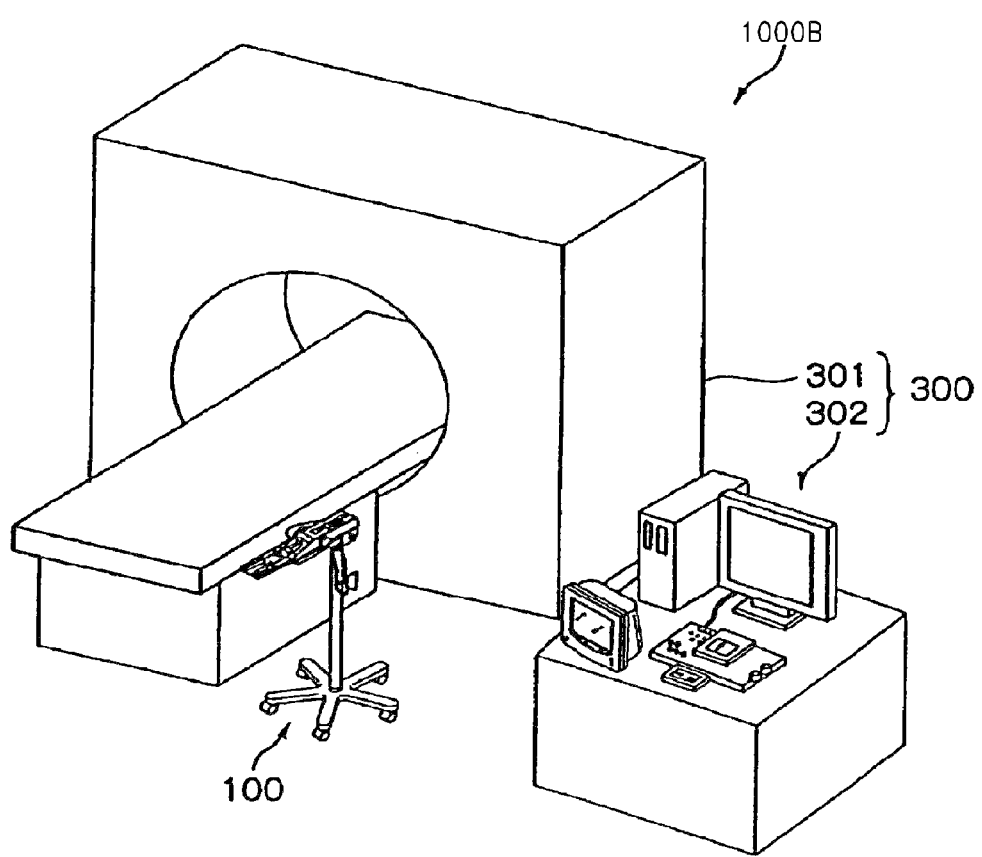
FIG. 3 is a perspective view showing an exterior appearance of the diagnostic imaging system.

The MRI apparatus 300 is provided with diagnostic imaging unit 301, which is an installation for implementing imaging, and imaging control unit 302, as shown in FIG. 3, with diagnostic imaging unit 301 and imaging control unit 302 wired-connected through communication network 303. Diagnostic imaging unit 301 shoots a diagnostic image of a patient, and imaging control unit 302 controls the operation of diagnostic imaging unit 301.

Figure 5:
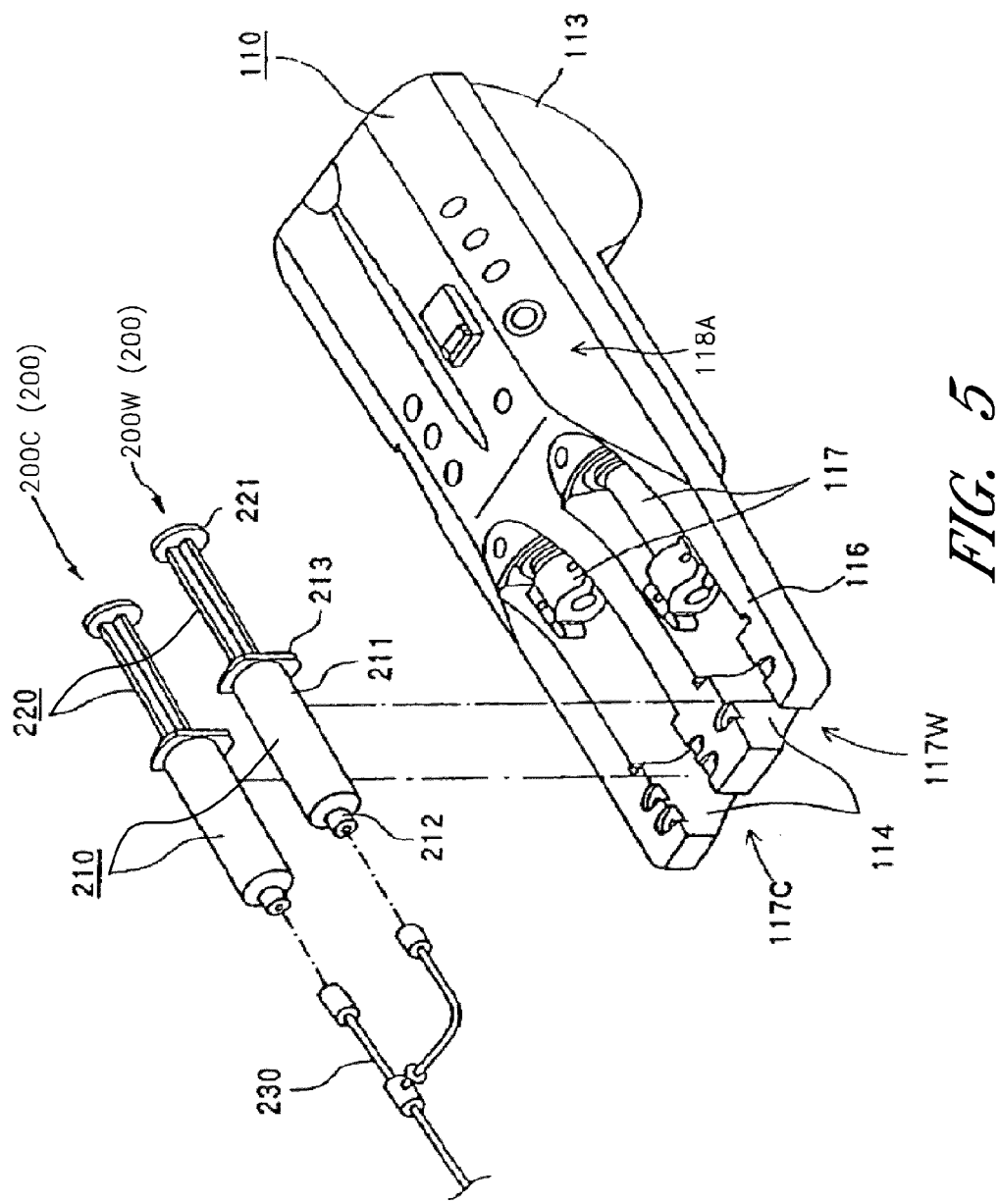
FIG. 5 is a perspective view showing a manner of mounting syringes on a injection head of the liquid injector.

Liquid syringe 200 comprises cylinder member 210 and piston member 220, wherein piston member 220 is slidably inserted into cylinder member 210, as shown in FIG. 5. Cylinder member 210 is provided with cylindrical hollow body 211, which has conduit tube 212 formed in the closed leading end surface.

The trailing end of body 211 of cylinder member 210 is opened and piston member 220 is inserted from the opening into the interior of body 211. Cylinder member 210 has cylinder flange 213 formed in the outer circumference of the trailing end, and piston member 220 has piston flange 221 formed in the outer circumference of the trailing end.

Figure 4:
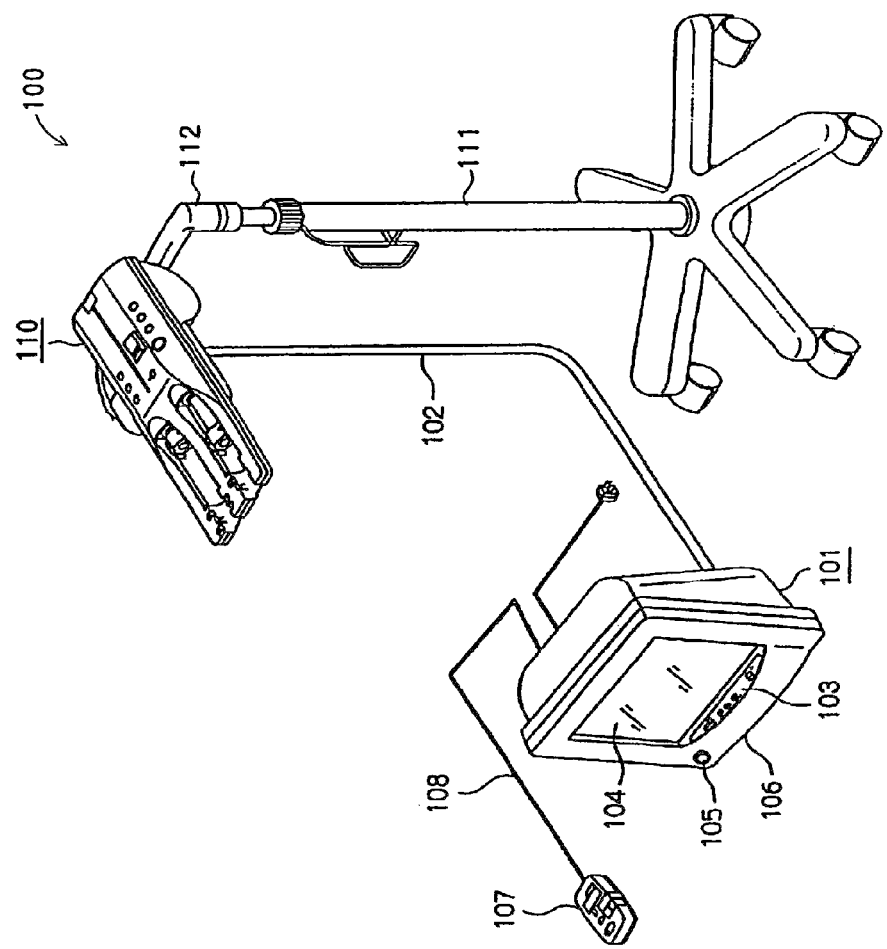
FIG. 4 is a perspective view showing an exterior appearance of the liquid injector.

As shown in FIG. 4, liquid injector 100 of the present embodiment has injection control unit 101 and injection head 110 constructed as separate units, which are wired-connected through communication cable 102.

Figure 2:
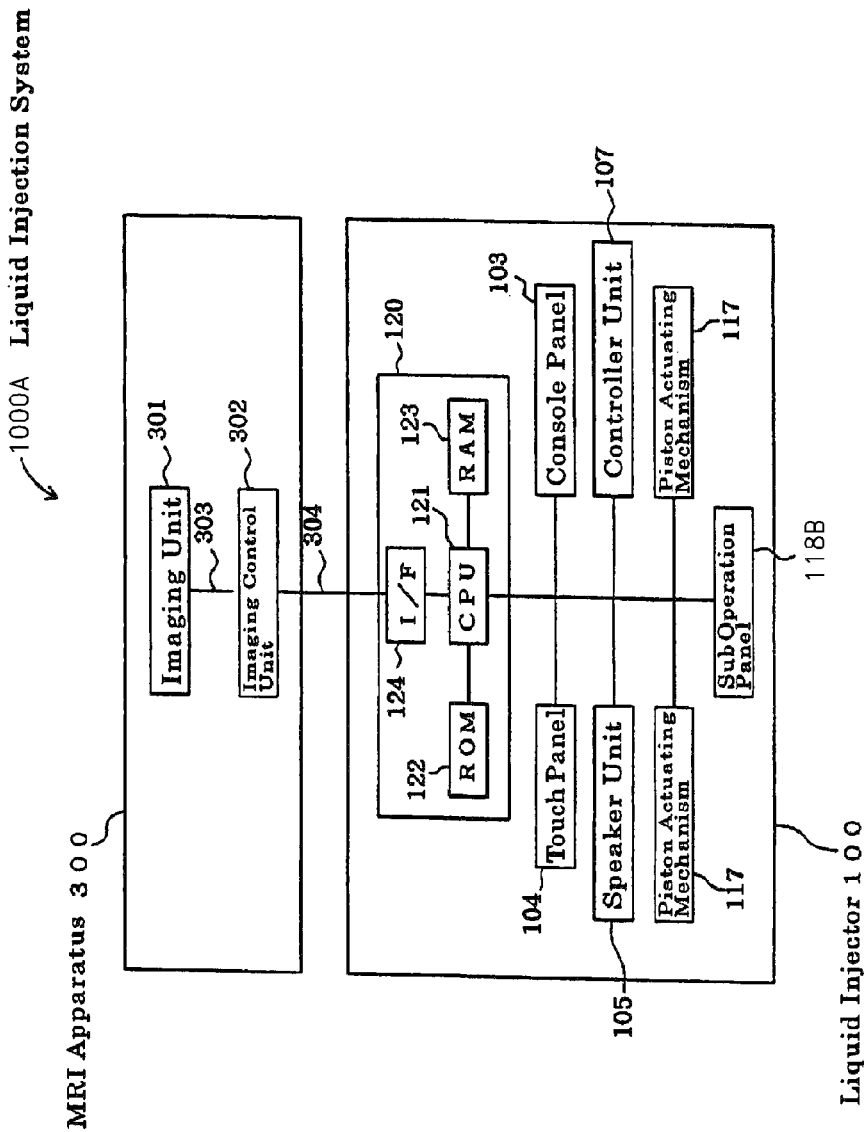
FIG. 2 is a block diagram showing a physical structure of the diagnostic imaging system.

Injection head 110 drives installed liquid syringe 200 to inject a liquid to a patient, and injection control unit 101 controls the operation of injection head 110. For this end, computer unit 120 is built in injection control unit 101 as shown in FIG. 2, and injection control unit 101 is wired-connected to imaging control unit 302 of MRI apparatus 300 through communication network 304.

Injection control unit 101 has main operation panel 103, main touch panel 104, which is a display panel, speaker unit 105, etc. arranged on the front face of main body housing 106 and is wired-connected via joining connector 108 to control unit 107, which is a separate unit.

Injection head 110 is attached to the top end of caster stand 111 with movable arm 112, and as shown in FIG. 4, head body 113, which is the injector body, has concave portions 114 formed in semi cylindrical grooves on the upper surface to adapt for removably attaching liquid syringe 200.

Concave portion 114 has cylinder-holding mechanism 116 for removably holding cylinder flange 213 of liquid syringe 200 formed in the forward section and also has piston actuating mechanism 117 for holding and slidingly moving piston flange 221 arranged in the rearward section.

Cylinder-holding mechanism 116 is formed in concave portions 114 in a form of an anomalous reentrant groove, with which each of cylinder flanges 213 removably engages. Piston actuating mechanisms 117 individually have motors as power sources and slidingly move piston members 220 through screw mechanisms or the like (not shown).

Because two concave portions 114 of injection head 110 are respectively adapted for receiving CM (contrast media) syringe 200C filled with a contrast media as a liquid and/or PS (physiological saline) syringe 200W filled with a physiological saline as a liquid, these two concave portions 114 and two piston actuating mechanisms 117 constitute both CM injection mechanism 117C for injecting a contrast media and PS injection mechanism 117W for injecting physiological saline, to a patient.

In addition, in liquid injector 100 of the present embodiment at least respective elements of injection head 110 are formed of nonmagnetic material, and the portions that cannot be formed of nonmagnetic material are magnetically shielded. For example, piston actuating mechanisms 117 individually have ultrasonic motors 118A, which are free from generation of magnetic field even when it is operated, as drive motors. Ultrasonic motors 118A are formed of nonmagnetic metals such as phosphor bronze alloy (Cu+Sn+P), titanium alloy (Ti—6A1—4V) and magnesium alloy (Mg+Al+Zn). Screw mechanisms of piston actuating mechanisms 117 and the like are formed of nonmagnetic metals and head body 113 and the like are formed of nonmagnetic resin.

In liquid injector 100 of the embodiment, computer unit 120 controls the operation of piston actuating mechanism 117 of injection head 110 in accordance with the manual operation on main operation panel 103 and/or touch panel 104 and/or controller unit 107 of injection control unit 101. However, injection head 110 has sub operation panel 118B formed on an upper surface of head body 113. Computer unit 120 also controls the operation of piston actuating mechanism 117 of injection head 110 in response to manual operation on sub operation panel 118B.

In addition, in liquid injector 100 of the present embodiment, computer unit 120 is made of a so-called one-chip microcomputer provided with hardware such as CPU (Central Processing Unit) 121, ROM (Read Only Memory) 122, RAM (Random Access Memory) 123, I/F (Interface) 124, etc.

Computer unit 120 has an appropriate computer program installed in an information storage medium such as ROM 122 as firmware or the like, and CPU 121 executes various processes in accordance with the computer program.

Figure 1:
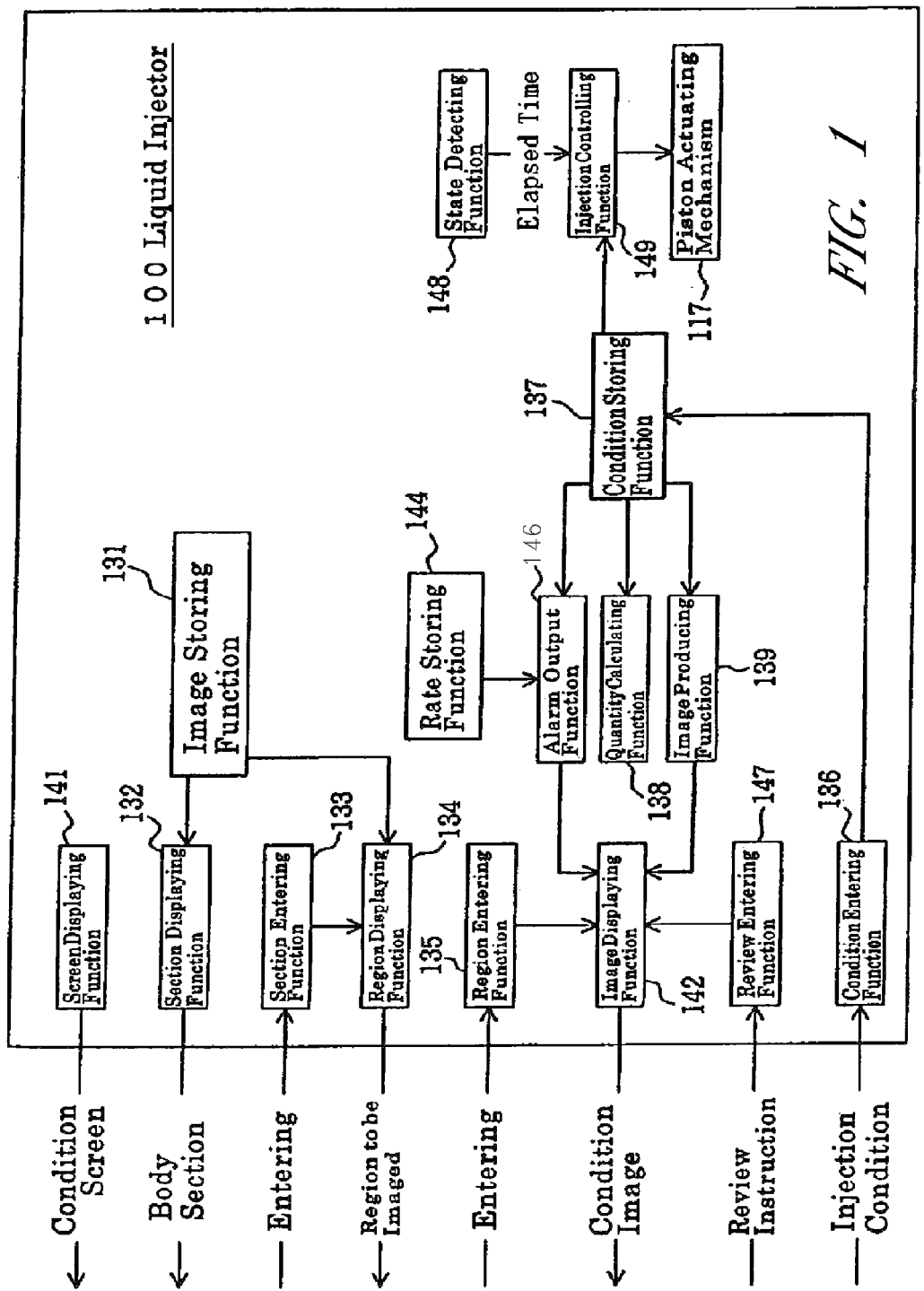
FIG. 1 is a schematic block diagram showing a logical structure of a liquid injector of a diagnostic imaging system of an embodiment according to the present invention.

By the operation of computer unit 120 in accordance with the computer programs installed therein as described above, liquid injector 100 of the embodiment has logically, as various means, various functions including image storing function 131, section displaying function 132, section entering function 133, region displaying function 134, region entering function 135, condition entering function 136, condition storing function 137, quantity calculating function 138, image producing function 139, screen displaying function 141, image displaying function 142, rate storing function 144, alarm output function 146, review entering function 147, state detecting function 148, and injection controlling function 149, as shown in FIG. 1.

Storing functions 131, 137, . . . correspond to storage areas set up in RAM 123 for CPU 121 to recognize data stored therein according to the computer program. Displaying functions 132, 134, . . . correspond to functions of CPU 121 to display stored data from RAM 123 on touch panel 104.

Entering functions 133, 135, . . . correspond to functions of CPU 121 to recognize data based on input actions on main/sub operation panels 103, 118B. Other various functions 138, 139, . . . correspond to functions of CPU 121 to process data.

Image storing function 131 stores data of schematic images of a plurality of body sections of a human body and data of schematic images of a number of regions to be imaged in relation to each other. Section displaying function 132 displays schematic images of body sections whose data are stored by image storing function 131 in the shape of a human body.

Section entering function 133 accepts an input action to select one of the body sections displayed by section displaying function 132. Region displaying function 134 displays a schematic image of at least one region to be imaged which corresponds to the body section selected by section entering function 133. Region entering function 135 accepts an input action to select the region to be imaged whose image has been displayed by region displaying function 134.

Figure 6:
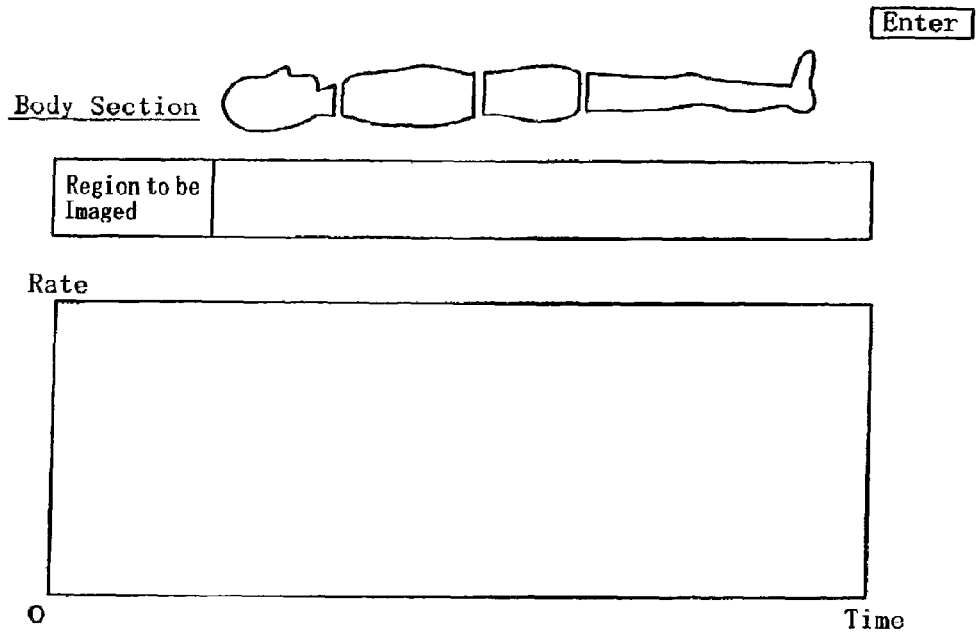
FIG. 6 is a schematic front view showing a displayed image at the time a schematic image of body sections and a condition screen with no data are displayed in the liquid injector.

More specifically, liquid injector 100 defines. "head part, chest part, abdomen part, and leg part" as a plurality of body sections, and data of schematic images corresponding to those body sections are registered in ROM 122. When a certain action is performed on liquid injector 100, schematic images of "head part, chest part, abdomen part, and leg part" in association with body shapes are displayed on an upper screen area of touch panel 104, as shown in FIG. 6.

Data of schematic images of "brain part, jaw part, and neck part" are registered as a plurality of regions to be imaged in relation to the schematic image of the body section "head part". Similarly, data of schematic images of "heart part and lung part" are registered in relation to the schematic image of the body section "chest part", data of schematic images of "stomach part, liver part, . . . " are registered in relation to the schematic image of the body section "abdomen part", and data of images of "upper part and lower part" are registered in relation to the schematic image of the body section "leg part".

Figure 7:
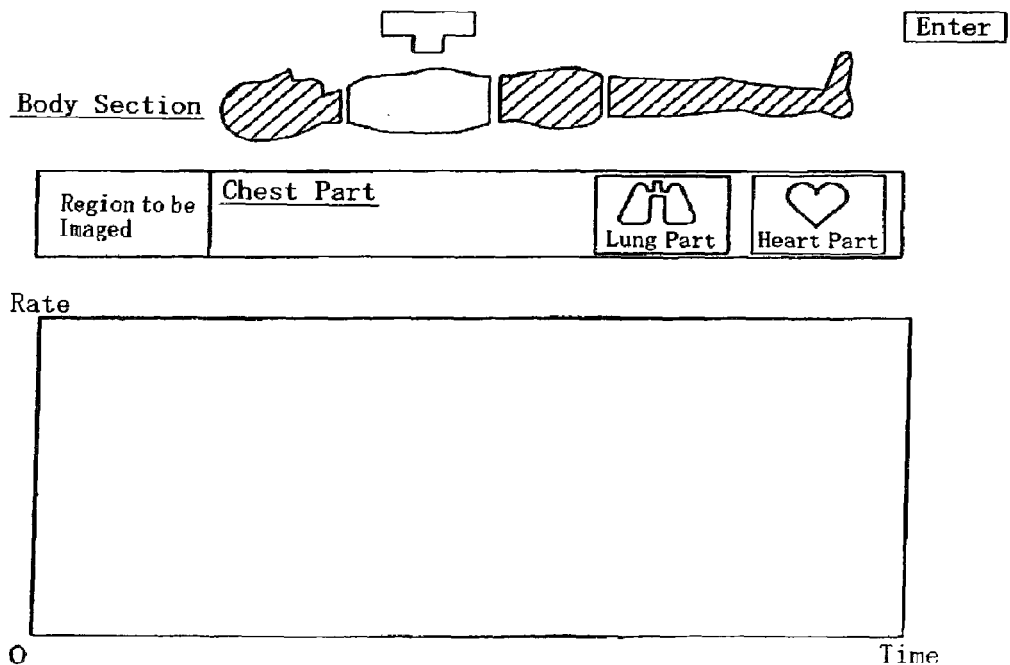
FIG. 7 is a schematic front view showing a displayed image at the time a body section is selected.
Figure 8:
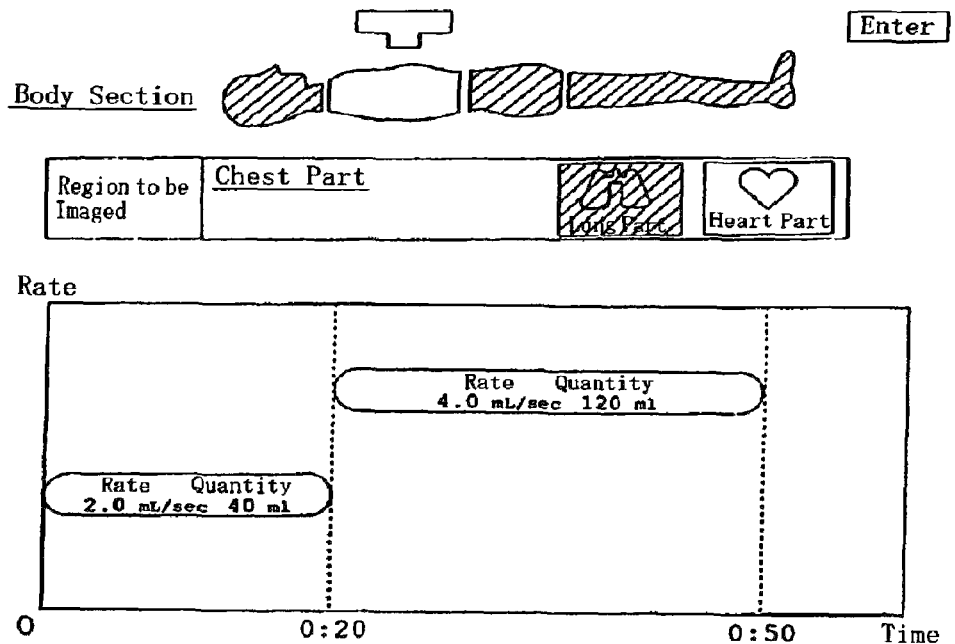
FIG. 8 is a schematic front view showing a displayed image at the time a region to be imaged is selected and a condition image is displayed.

When one of the schematic images of the body sections displayed as a human body shape on touch panel 104 is manually acted upon, a schematic image of a scanner mechanism is displayed above only the schematic image that is acted upon, and that schematic image is highlighted with the other schematic images darkened, as shown in FIG. 7. At the same time, the schematic images of the regions that are related to the highlighted image are displayed below the displayed schematic images of the body sections. When one of the displayed schematic images of the related regions is manually acted upon, that schematic image is highlighted with the other schematic images darkened, as shown in FIG. 8.

Condition entering function 136 accepts an input action of an injection condition including an injection rate for each of injection time periods of a contrast media and a physiological saline for the region to be imaged selected by region entering function 135. Condition storing function 137 stores the injection condition entered by condition entering function 136 for each region to be imaged.

Quantity calculating function 138 calculates the injection quantity from the injection time period and the injection rate for each injection condition stored by condition storing function 137. Image producing function 139 produces a condition image having a horizontal width corresponding to the injection time period and including text data which represents the injection rate and the injection quantity for each stored injection condition.

As shown in FIG. 6, screen displaying function 141 displays a horizontally rectangular condition screen with its vertical axis representing the injection rate of the liquid and its horizontal axis representing the injection time period. As shown in FIG. 8, image displaying function 142 displays the condition image produced by image producing function 139 in the condition screen at the vertical position in association with the injection rate and the horizontal position in association with the injection time period.

In liquid injector 100 of the embodiment, the injection conditions for the contrast media and the physiological saline are individually entered as described above, so that the condition images thereof are produced in different colors such as green and blue, and the condition images are arranged horizontally and displayed in the condition screen.

In addition, when the plurality of condition images are arranged horizontally and displayed, a line segment is displayed at the position of the border between them, and numerical values of the injection time are displayed as text data at the lower end of the line segment. Thus, when a first injection time period is "20 (sec)" and a second injection time period is "30 (sec)," a first injection time and a second injection time are displayed as "20 (sec)" and "50 (sec)," respectively.

Condition storing function 137 stores a default injection condition in advance for each region to be imaged even when no injection condition is entered by condition entering function 136. It also stores the previous injection condition entered by condition entering function 136 for each region to be imaged.

Thus, in liquid injector 100 of the embodiment, when a region to be imaged is selected as described above, a condition image with the previous injection condition, if stored, is produced and displayed even when no injection condition is entered for the current injection. If the previous injection condition is not stored, a condition image with the default injection condition is displayed.

The input action of the injection condition by condition entering function 136 is performed, for example, by entering numerical values on operation panel 103, and also performed by directly acting upon a condition image displayed on touch panel 104. In this case, the operator can touch the center of the displayed condition image with a fingertip to move the condition image upward and/or downward with the fingertip to increase and/or reduce the injection rate of the injection condition.

In addition, the operator can touch at least one of both lateral ends of the displayed condition image with a fingertip and moves the fingertip leftward and/or rightward to increase and/or reduce the injection time period and/or the injection quantity of the injection condition. When the operator touches with a fingertip the numerical values of the injection rate or the injection quantity of the displayed condition image, an image of a numeric keypad is displayed there (not shown), and the operator can increase and/or reduce the injection rate and/or the injection quantity by manually operating the numeric keypad. Then, the data of the stored injection condition is updated in response to the manual operation of the condition image as described above, and the data of the displayed condition image is updated in real time.

Rate storing function 144 stores the upper limit rate of liquid injection in advance. Alarm output function 146 outputs an alarm when the injection rate of the injection condition stored by condition storing function 137 exceeds the upper limit rate. More specifically, the upper limit rate is registered as data for each region to be imaged and each type of liquid, and is read out in association with the selected region to be imaged and type of liquid. The condition image which includes the injection rate exceeding the upper limit rate blinks in a dedicated color such as red, and a predetermined guidance message as "critical rate" is provided as alarm display.

Figure 9:
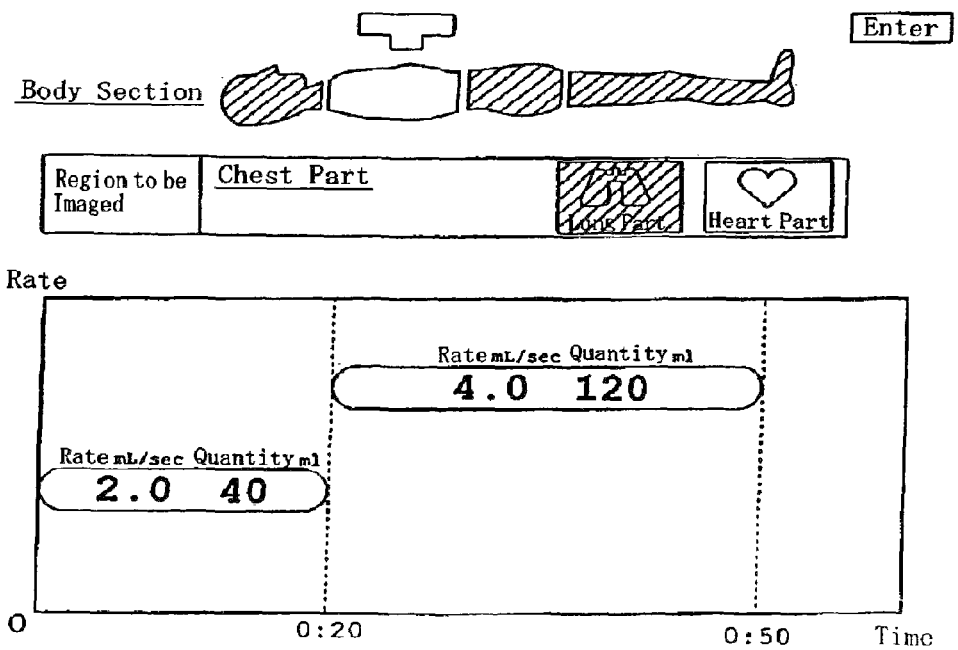
FIG. 9 is a schematic front view showing a displayed image at the time text data of the region to be image is enlarged.

Review entering function 147 accepts an input action of a review instruction. As shown in FIG. 9, image displaying function 142 enlarges text data of the condition image when the review instruction is entered. The review instruction may be entered on touch panel 104 on which the injection condition is displayed, but it is normally entered on sub operation panel 118B of injection head 110 separate from touch panel 104.

As shown in FIG. 8, the condition image is displayed as a horizontal rectangle having semicircular shape at both ends in the embodiment. Generally, item names as "rate" "quantity" are displayed as text data at predetermined positions in upper portions inside the rectangle, and the numerical values and their units as "2.0 mL/sec" "4.0 ml" are displayed as text data under the associated item names.

However, when the review instruction is entered as described, as shown in FIG. 9, the text data representing the item names as "rate" and the units as "mL/sec" are displayed over the condition image, and only the text data representing the numerical values as "2.0" is enlarged in the condition image.

When liquid injection is performed in response to manual operation on touch panel 104 or the like, state detecting function 148 measures the elapsed time from the start of the injection. Injection controlling function 149 sequentially controls the operation of the plurality of piston actuating mechanisms 117 in real time based on the elapsed time measured by state detecting function 148 and the plurality of stored injection conditions.

While the above various functions of liquid injector 100 are accomplished by pieces of hardware such as touch panel 104, if necessary, they are mainly implemented by CPU 121 as a piece of hardware as it functions according to resources stored in an information storage medium such as ROM 122, etc., and the computer program.

Such resources are formed of, for example, a data file including schematic images of a plurality of body sections of a human body and schematic images of a number of regions to be imaged in relation to each other, a data file including injection conditions of CM/PS injection mechanisms 117C and 117W for each of the number of regions to be imaged of a human body, a data file including the upper limit rates of CM/PS injection mechanisms 117C, 117W for each region to be imaged, or the like.

The abovementioned computer program is stored in an information storage medium such as RAM 123 as software for causing CPU 121 or the like to perform processing operations such as display of schematic images of the plurality of body sections registered as data in RAM 123 or the like in the shape of a human body on touch panel 104 and display of a condition screen of horizontal rectangle, under the schematic images, with the vertical axis representing the injection rate of the liquid and the horizontal axis representing the injection time period, reception of an input action on touch panel 104 to select one of the plurality of body sections displayed as the image, display of the schematic image of at least one region to be imaged in association with the selected body section, reception of an input action to select the region to be imaged displayed as the image, display of the injection condition registered as data in association with the selected region to be imaged together with the condition screen, reading of the previous injection conditions of the contrast media and physiological saline for the selected region to be imaged from RAM 123 or the like, reading of the default injection condition when the previous injection condition is not stored, calculation of the injection quantity from the injection time period and the injection rate for each of the stored injection conditions, production of the condition image having the horizontal width corresponding to the injection time period and including the injection rate and the injection quantity as text data for each of the stored injection conditions, display of the produced condition image in the injection screen at the vertical position in association with the injection rate and the horizontal position in association with the injection time period, reception of an input action of the injection condition as edit operation of the displayed condition image, storage of the newly input injection condition to reflect it on the data production for the condition image and display thereof, output of an alarm when the injection rate of the stored injection condition exceeds the upper limit rate, enlargement of the text data of the condition image displayed on touch panel 104 when a review instruction is entered on the sub operation panel 118B or the like, performance of the liquid injection in response to manual operation on touch panel 104 or the like, calculation of the elapsed time from the start of the injection, and sequential control of the operation of the plurality of piston actuating mechanisms 117 in real time based on the elapsed time and the plurality of stored injection conditions.

"Operation of Embodiment"

For using liquid injector 100 of the above construction, the operator (not shown) positions liquid injector 100 near imaging unit 301 of MRI apparatus 300 as shown in FIG. 3. Then, as shown in FIG. 5, the operator connects liquid syringes 200C, W of a contrast media and a physiological saline to the patient (not shown) placed in imaging unit 301 with bifurcated extension tube 230. Cylinder members 210 of liquid syringes 200 are held in respective concave portions 114 of injection head 110, and piston members 220 are gripped by piston actuating mechanisms 117.

Figure 10:
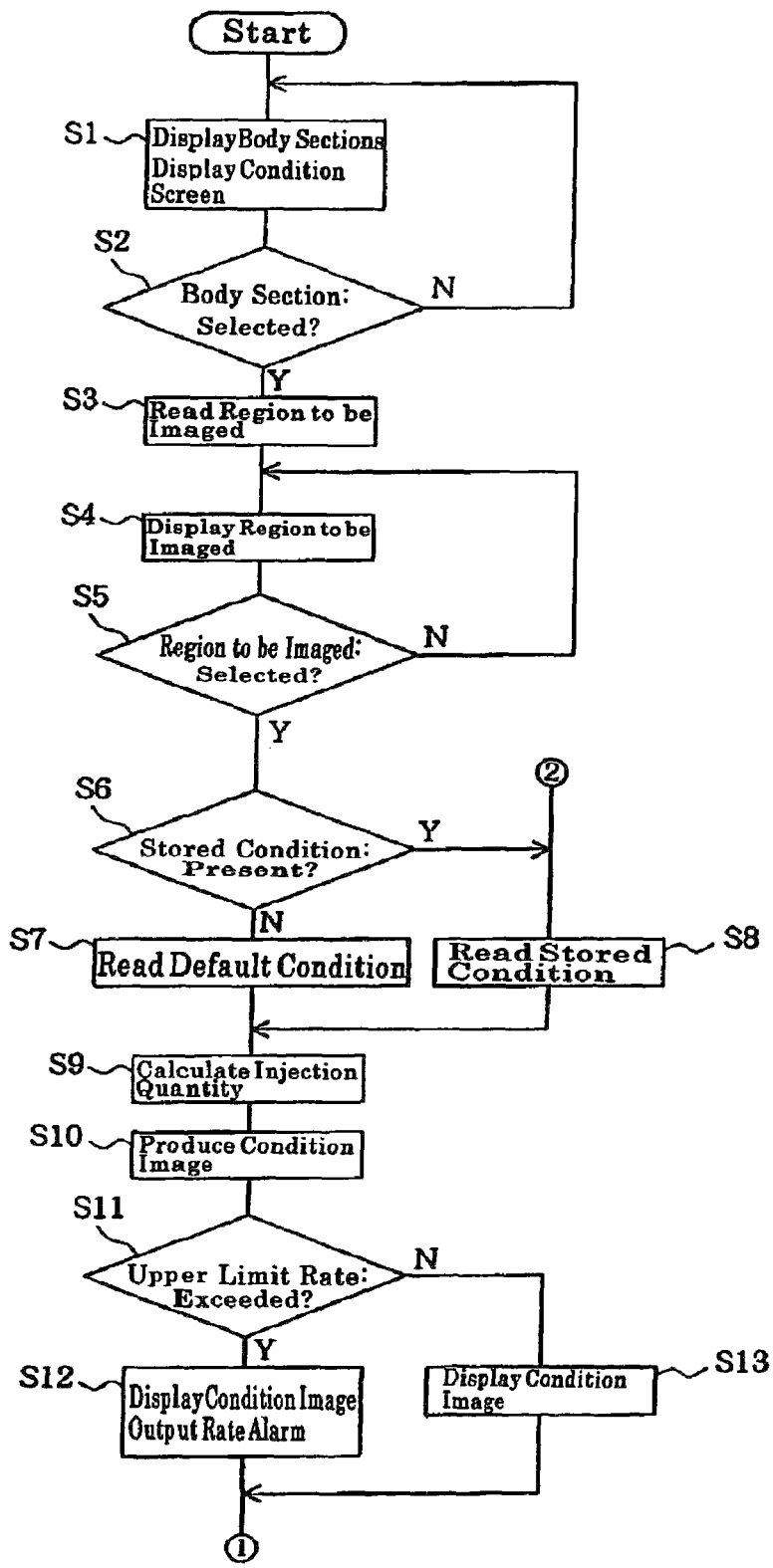
FIG. 10 is a flowchart of a first part of a processing sequence of the liquid injector.

Next, the operator activates liquid injector 100 by an input action on main operation panel 103 or the like. Then, as shown in FIGS. 6 and 10, schematic images of a plurality of body sections are displayed in the shape of a human body in an upper portion of touch panel 104, and under the schematic images, a horizontally rectangular condition screen is displayed with the vertical axis representing the injection rate of the liquid and the horizontal axis representing the injection time period (Step S1).

If the operator touches, with a fingertip, one of the schematic images of the body sections displayed on touch panel 104 to select the touched schematic image of the body section (Step S2), then, as shown in FIG. 7, the selected schematic image of the body section is highlighted with the other schematic images darkened, and a schematic image of a scanner mechanism is also displayed above the selected schematic image of the body section.

At the same time, schematic images of a plurality of regions to be imaged which are related to the selected body section are read and displayed below the displayed schematic images of the body sections (Steps S3, S4). If the operator touches one of the schematic images of the regions to select the touched schematic image of the region (Step S5), then only the selected schematic image of the region is highlighted with the other schematic images darkened, as shown in FIG. 8.

When the region to be imaged is selected as described above, liquid injector 100 of the embodiment checks whether the previous injection condition associated with the selected region to be imaged is registered as data in RAM 123 (step S6). If the data is not registered, the default injection condition is read out (step S7). If the data is registered, the previous injection condition is read out (step S8). In liquid injector 100 of the embodiment, the contrast media and the physiological saline are basically injected sequentially, so that the injection conditions of the contrast media and the physiological saline are registered in association with a region to be imaged, and these injection conditions are read out.

Since the injection conditions thus read out include the injection time period and the injection rate set as data, the injection time period is multiplied by the injection rate to calculate the injection quantity for each injection condition (step S9). Then, the condition image is produced for each injection condition to have a horizontal width corresponding to the injection time period and to include the injection rate and injection quantity as text data (step S10). As shown in FIG. 8, the condition image is displayed in the condition screen at the vertical position in association with the injection rate and the horizontal position in association with the injection time period (steps S12, S13).

At this point, since the condition images are produced from the injection conditions of the contrast media and physiological saline as described above, the condition images are displayed in green and blue, respectively, and arranged horizontally. It is determined whether or not the injection rate exceeds the upper limit rate for each injection condition (step S11). For the injection condition with the excessive injection rate, the condition image blinks in red to output a rate alarm (step S12).

Figure 11:
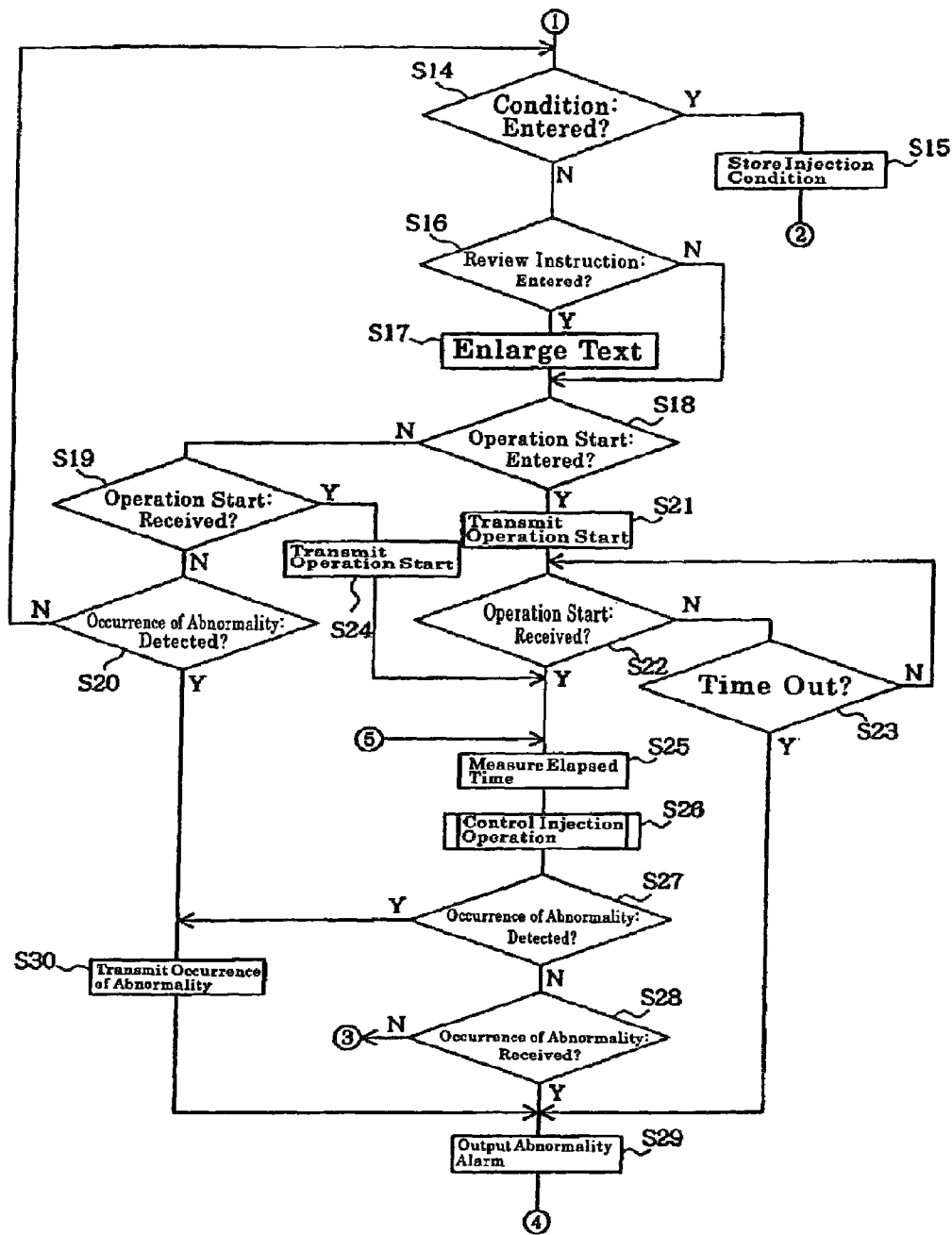
FIG. 11 is a flowchart of a mid part of the processing sequence of the liquid injector.
Figure 12:
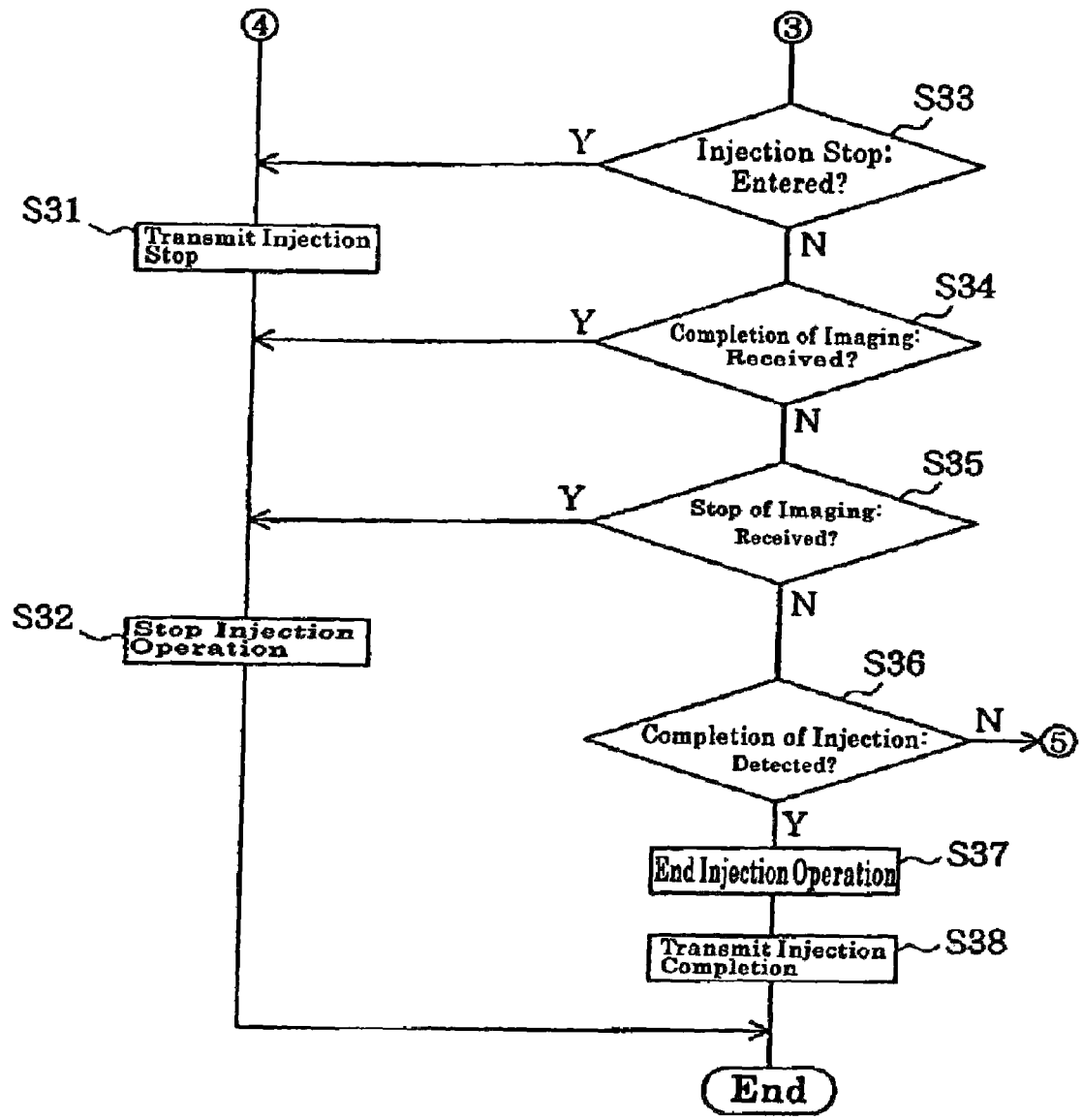
FIG. 12 is a flowchart of a last part of the processing sequence of the liquid injector.

As shown in FIG. 11, liquid injector 100 of the embodiment can start injection operation in the abovementioned state (step S18 and after), later described in detail. However, the injection condition can be changed as desired (steps S13, A14). In that case, for example, the operator can touch the center of the condition image displayed on touch panel 104 with a fingertip to move the condition image upward and/or downward with the fingertip to increase and/or reduce the injection rate of the injection condition.

In addition, the operator can touch at least one of both of lateral ends of the displayed condition image with a fingertip and moves the fingertip leftward and/or rightward to increase and/or reduce the injection time period and/or the injection quantity of the injection condition. When the operator touches with a fingertip the numerical values of the injection rate and/or the injection quantity of the displayed condition image, an image of a numeric keypad is displayed there (not shown), the operator can increase and/or reduce the injection rate and/or the injection quantity by manually operating the numeric keypad.

When the condition image is manually acted upon to enter the injection condition in this manner (step S14), that is stored as the current injection condition (step S15), and the data production of the condition image is performed in real time (steps S8 to S14).

In the normal operation using liquid injector 100, the operator checks the mounting of liquid syringe 200 on injection head 110, the coupling of liquid syringe 200 to extension tube 230 to the patient, or the like, before liquid injection is started. When liquid injector 100 is used near MRI apparatus 300, only injection head 110 is placed near diagnostic imaging unit 301 of MRI apparatus 300 and injection control unit 101 is placed at a position away therefrom, in view of the influence on the magnetic field.

When the operator performs check operation near injection head 110 before liquid injection is started, the operator stays away from injection control unit 101, so that it is not easy to visually check the injection condition of the condition image displayed on touch panel 104.

Thus, when the operator wishes to review the injection condition, the operator enters a review instruction on sub operation panel 118B of injection head 110 (step S16). Then, as shown in FIG. 9, text data of the numerical values of the injection rate and injection quantity displayed in the condition image is enlarged (step S17). The operator can easily review the injection condition of the condition image displayed on touch panel 104 of injection control unit 101.

Figure 13:
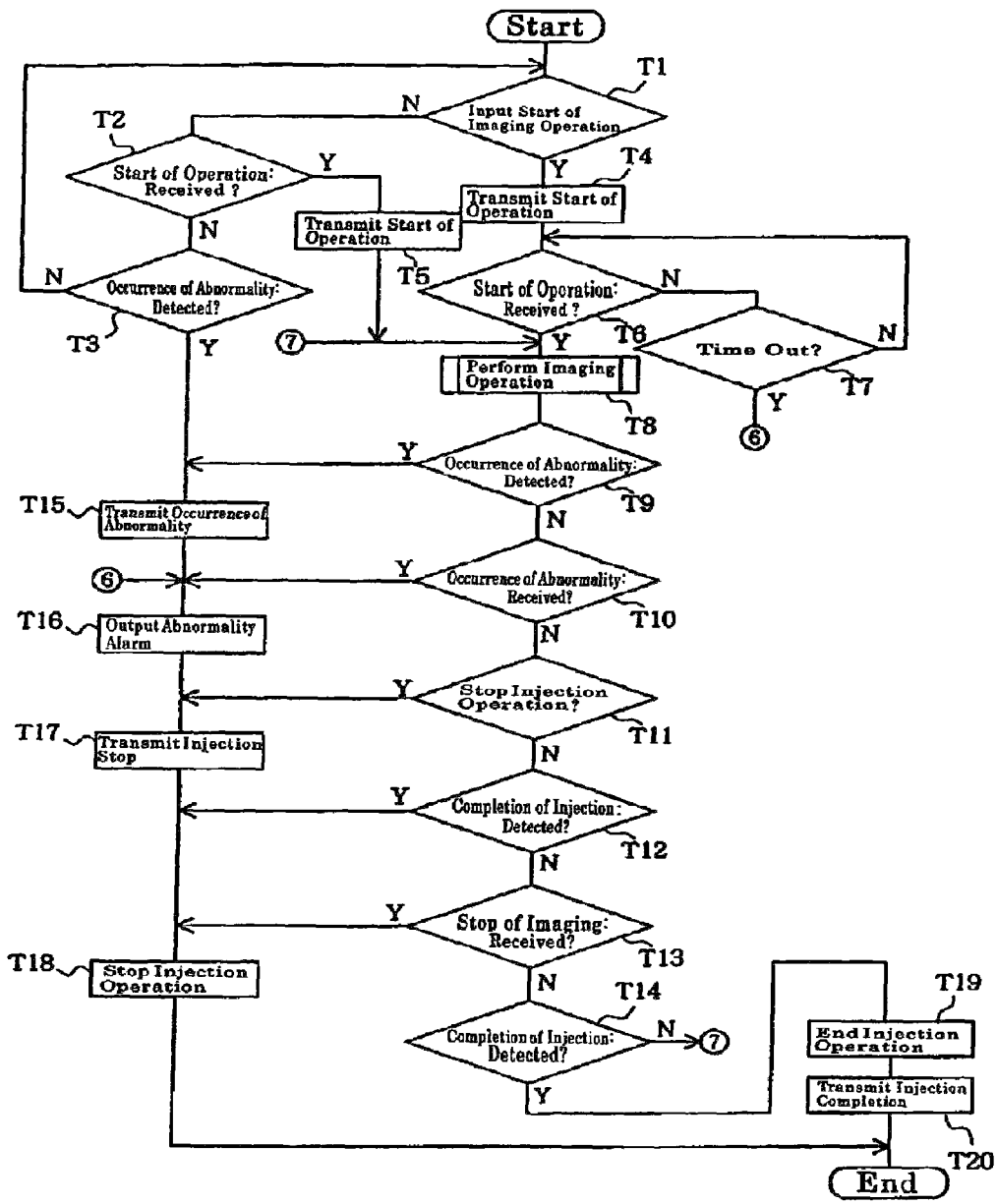
FIG. 13 is a flowchart of the processing sequence of the MRI apparatus as an imaging diagnostic apparatus.

When the operator makes an input action to start the operation on operation panel-103 of liquid injector 100 with the preparation for injection operation completed as described above, liquid injector 100 senses it and sends data to start operation to MRI apparatus 300 (steps S18, S21). As shown in FIG. 13, MRI apparatus 300, upon reception of the data to start the operation from liquid injector 100 (step T2), sends data to start the operation back to liquid injector 100 and performs imaging operation (step T8).

As shown in FIG. 11, liquid injector 100, to which the data to start the operation is sent back from MRI apparatus 300 (step S22), performs a series of liquid injection operations (step S25 and after). In this case, the elapsed time after the start of the injection is measured (step S25). The operations of CM injection mechanism 117C and PS injection mechanism 117W are sequentially controlled in real time based on the elapsed time and the read injection condition (step S26).

For this end, the imaging operation of MRI apparatus 300 follows up the liquid injection made by liquid injector 100 in the diagnostic imaging system 1000B of this embodiment. For reference, in diagnostic imaging system 1000B of the present embodiment, when liquid injector 100 is in ready state as described above (Steps S14 to S20) and an input operation is made to command MRI apparatus 300 to start an imaging operation (Step T1) as shown in FIG. 13, liquid injection of liquid injector 100 follows up the diagnostic imaging of MRI apparatus 300 (Steps T4, T6, -, S19, S24, -).

Further, in liquid injector 100 and MRI apparatus 300 of the present embodiment, if an occurrence of abnormality is detected in ready state described above (Steps S20, T3), or if an occurrence of abnormality is detected in the course of making an operation (Steps S27, T9), the occurrence of abnormality is notified (Steps S29, T16) and also a break of the operation is executed (Steps S32, T18).

Since the occurrence of abnormality is notified also to another apparatus (Steps S30, T15), the other apparatus that receives the notification of the occurrence of abnormality (Steps T10, S28) also provides a notification of the occurrence of abnormality (Steps T16, S29). Further, since a break of an operation in one apparatus is also notified to another apparatus (Steps S31, T17), the other apparatus that receives the notification of the break of the operation (Steps T13, S35) also executes a break of an operation (Steps T18, S32).

Furthermore, when an input operation is made in one apparatus to command to break an operation (Steps S33, T11), the beak of an operation is executed in the apparatus of interest (Steps S32, T18) and also notified to another apparatus (Steps S31, T17). As a result, the beak of an operation is executed (Steps T18, S32) in the other apparatus that receives the notification (Steps T13, S35).

Furthermore, when the completion of the operation is detected in one apparatus (Steps S36, T14), the completion of the operation is executed in the apparatus of interest (Steps S37, T19) and also notified to another apparatus (Steps S38, T20). As a result, the completion of the operation is executed (Steps T18, S32) in the other apparatus that receives the notification (Steps T12, S35)

"Effect of the Embodiment"

As shown in FIG. 8, in liquid injector 100 of the embodiment, the condition image for the injection condition including the injection rate as text data and having the horizontal width corresponding to the injection time period is displayed in the condition screen with the vertical axis representing the injection rate and the horizontal axis representing the injection time period at the vertical position in association with the injection rate and the horizontal position in association with the injection time period. Thus, the operator easily understands instinctively the injection condition from the horizontal width and the position of the condition image, and also, since the text data of the injection rate is included in the condition image, the operator can quickly review the numeric values.

In addition, in liquid injector 100 of the embodiment, the operation of piston actuating mechanism 117 is controlled in real time based on the injection condition and the elapsed time, so that the liquid can be injected to the patient at the appropriate rate for the appropriate time period. Particularly, since the injection conditions of the contrast media and physiological saline are automatically arranged sequentially, CM/PS injection mechanisms 117C, 117W can automatically be operated sequentially to inject the contrast media and physiological saline into the patient in an appropriate order.

Since only the injection time period and the injection rate are necessary for the input action of the injection condition, the input action is simple and easy. Particularly, the injection condition can be registered as data for each region to be imaged of a human body, and when a region to be imaged is selected by an input action, the previous injection condition is automatically read out to display the condition image including that injection condition, so that the injection condition does not need to be entered each time, and the liquid can be injected under an appropriate condition for each region to be imaged.

When the previous injection condition is not registered as data, the default injection condition is read out to display the condition image including the default condition, the liquid can be injected under an appropriate injection condition for each region to be imaged even when the injection condition is not entered. The input action of the injection condition can be performed by manually acting upon the displayed previous condition image or default condition image, so that the input action is extremely simple and easy.

Particularly, since the condition image is display on touch panel 104 and manually acted upon, the operator can directly act upon the condition image manually. Also, the operator can touch the center of the displayed condition image with a fingertip to move the condition image upward and/or downward with the fingertip to increase and/or reduce the injection rate of the injection condition, so that the injection rate can be changed simply and easily.

In addition, the operator can touch at least one of both of lateral ends of the displayed condition image with a fingertip and moves the fingertip leftward and/or rightward to increase and/or reduce the injection time period and the injection quantity of the injection condition. Thus, the injection time period and the injection quantity can be changed simply and easily. When the operator touches with a fingertip the numerical values of the injection rate and the injection quantity of the displayed condition image, an image of a numeric keypad is displayed there, the operator can manually operate the numeric keypad to simply and easily change the injection rate and the injection quantity.

In addition, when the injection rate and the injection time period are entered as described above, the injection quantity is automatically calculated and provided as text data in the condition image, so that the operator can see the injection quantity only by entering the injection rate and the injection time period. Also, when the operator enters a review instruction to liquid injector 100, the text data of the condition image is enlarged, so that the operator can favorably review the injection rate and the injection quantity.

Particularly, in liquid injector 100 of the embodiment, injection control unit 101 on which the condition image is displayed is separate from injection head 110 on which the check operation is performed, but when a review instruction is entered to injection head 110, the text data of the condition image displayed on injection control unit 101 is enlarged, so that the operator performing the check operation on injection head 110 can favorably review the injection rate and the injection quantity of the injection condition displayed on injection control unit 101.

As shown in FIG. 8, the text data of the condition image is produced as a combination of the numeric value with its unit. However, as shown in FIG. 9, only the text data of numerical value is enlarged and the text data of the unit is displayed outside the condition image. Thus, only the required information can be enlarged without unnecessarily enlarging the whole condition image.

Since liquid injector 100 of the embodiment displays the condition images of the contrast media and the physiological saline in individually dedicated colors, the operator can make a clear distinction between the injection conditions of the contrast media and the physiological saline. In addition, since the rate alarm is output when the injection rate of the injection condition exceeds the upper limit rate, it is possible to prevent the liquid from being injected into the patient at a critical rate.

Specifically, since the rate alarm is performed by displaying the condition image in the alarm color and blinking it, it is possible to simply and reliably notify the operator that the injection rate is a critical rate. In addition, the injection conditions of the contrast media and the physiological saline are normally displayed in blue and green, but they are displayed in the complementary color or red when the rate thereof is at a critical rate, so that the operator can be notified clearly that the injection rate is a critical rate.

In liquid injector 100 of the embodiment, the schematic images of a plurality of body sections are displayed in the shape of a human body on touch panel 104. When the operator manually acts upon one of them as desired, the schematic images of the plurality of regions to be imaged associated with the body section acted upon are displayed. When the operator manually acts upon one of them as desired, one region to be imaged is selected. Thus, the selection of a region to be imaged for use in data registration or data reading for the injection condition can be performed reliably with simple operation.

Since liquid injector 100 displays schematic images of a plurality of body sections in the shape of a human body, the operator is allowed to select any of the body sections easily and reliably. Because schematic images of body sections and regions to be imaged are displayed on touch panel 104 and can directly be manually acted upon, they can be touched and selected easily and reliably.

Still further, in liquid injection system 1000A of the present embodiment, since the liquid injection performed by liquid injector 100 and the shooting of images made by MRI apparatus 300 are automatically linked to each other, it is enabled to shoot in appropriate timings diagnostic images from the patient, who has had sequential injection treatments of a contrast media and a physiological saline in proper timings, "Modifications of Embodiment"

The present invention is not in any way limited to the above-described embodiment, but various changes or modifications may be made therein without departing from the scope of the invention. For example, although liquid injector 100 according to the above embodiment has CM and PS injection mechanisms 117C, W for injecting a contrast media and a saline solution, the present invention is also applicable to a liquid injector having a single piston actuating mechanism 117 for injecting a contrast media only (not shown).

Figure 14:
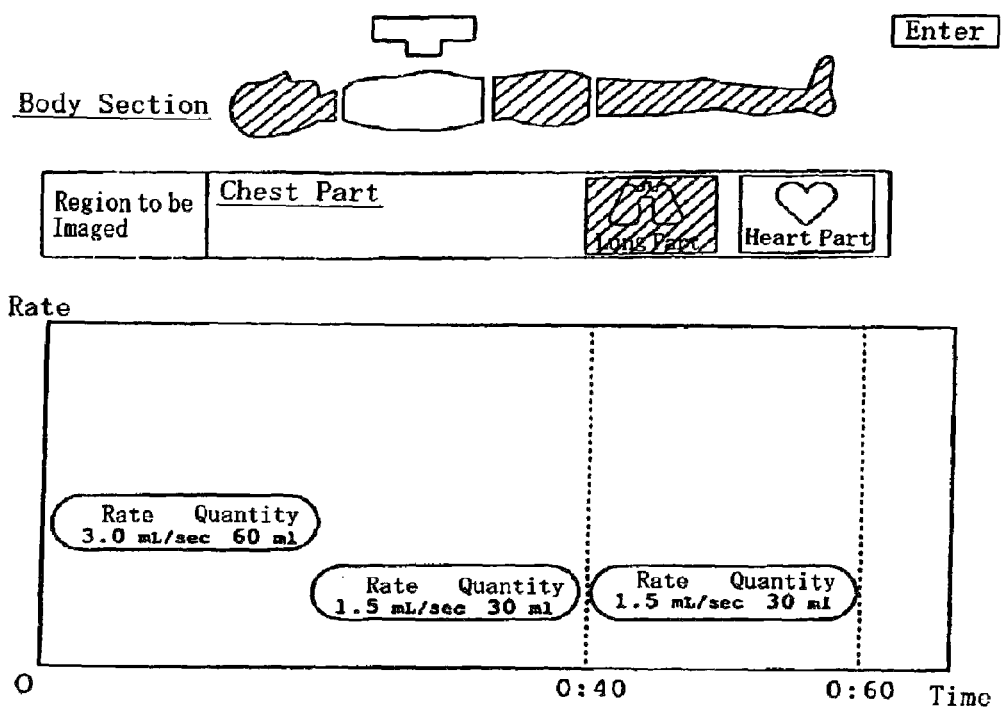
FIG. 14 is a schematic front view showing a displayed image of the liquid injector according to a modification of the present invention.

In liquid injector 100 of the above embodiment, a single injection condition is entered for a single liquid. However, as shown in FIG. 14, a plurality of injection conditions can be entered for a single liquid. In this case, since the injection rate of the contrast media can be variable in a plurality of levels, the injection operation can be performed more precisely. In addition, the liquid injection can be automatically stopped temporarily for a predetermined time period by inserting the injection rate of "zero" into the plurality of injection conditions.

Although the input action of the injection condition and the image display are simultaneously performed on touch panel 104 in the above embodiment, it is possible that a display panel and a pointing device as separate units are used to perform image display and an input action of the injection condition respectively (not shown), for example.

In the above embodiment, the condition screen and/or the schematic images of body sections registered electronically as data are displayed on touch panel 104. However, the condition screen and/or the schematic images of body sections can be formed fixedly, for example by painting at a predetermined position on the surface.

In the above embodiment, the data of an injection condition for each region to be imaged is registered, and then read for a desired region to be imaged for controlling the injection of a liquid. There are various other conditions than the selection of a region to be imaged for an optimum injection of a liquid such as a contrast media.

For example, the actual contrast media for use on MRI apparatus 300 contains an effective component of iodine whose concentration differs from product to product. Imaging conditions differ with body weights of patients to be imaged. As disclosed in Japanese patent application No. 2003-039756 filed by the present applicant, the data of the weight of a patient and the type of a contrast media used may be entered into the liquid injector, and an injection condition may be adjusted depending on the entered data.

In the above embodiment, a contrast media and a saline solution are sequentially injected according to an injection condition. However, as disclosed in Japanese patent application No. 2002-363675, it is possible to dilute a contrast media with a saline solution and inject the diluted contrast media according to an injection condition.

In the above embodiment, the injection condition is entered manually to liquid injector 100. The data of the injection condition may be registered on an information storage medium such a PC card in advance and the injection condition may be downloaded from the information storage medium to liquid injector 100.

The data of an injection condition may be registered in an external database server, and liquid injector 100 may download the registered data on-line from the external database server. Similarly, the data of an injection condition may be registered in a host computer of the manufacturer of liquid injector 100, and liquid injector 100, which is installed in a medical facility, may download the registered data from the host computer through the Internet.

In the above embodiment, the data of the default injection condition recommended by the manufacturer is registered in liquid injector 100. However, it is possible to manufacture and sell liquid injector 100 with no injection condition registered. In addition, although liquid injector 100 stores and automatically displays the previous injection condition in the above embodiment, such data storage may not be performed, and the data of the injection conditions provided from several injections may be stored and selectively displayed by manual operation.

Figure 15A:
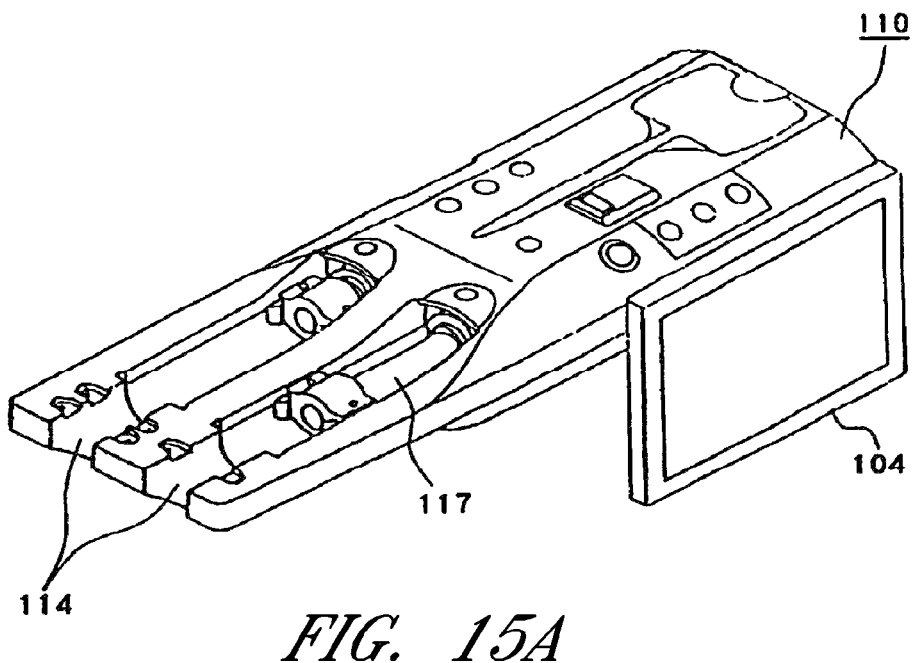
FIGS. 15a and 15b are perspective views showing injection heads of liquid injectors according to second modifications of the present invention.
Figure 15B:
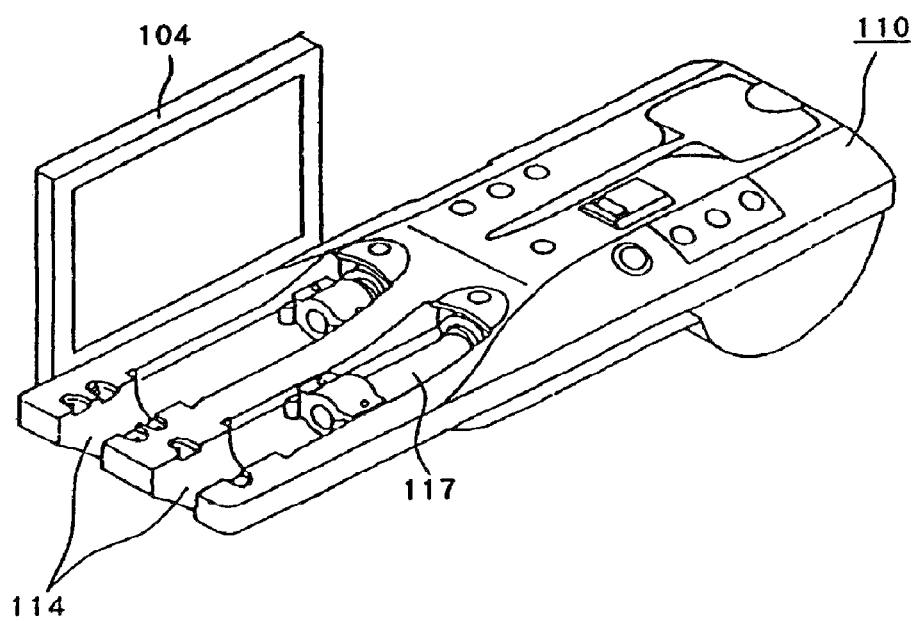

In the above embodiment, touch panel 104 is mounted on the upper surface of injection control unit 101 of liquid injector 100, and injection head 110 is mounted on the upper end of movable arm 109 which is vertically mounted on the side wall of injection control unit 101. However, as shown in FIGS. 15a and 15b, touch panel 104 may directly be connected to injection head 110 parallel thereto.

Since touch panel 104 is positioned adjacent to CM and PS injection mechanisms 117C, W, the operator can directly and easily recognize entered injection conditions when the injection conditions for CM and PS injection mechanisms 117C, W are displayed on touch panel 104.

In the above embodiment, the horizontal axis of the condition screen represents the injection rate, and the injection condition is made up of the injection rate and the injection time period. The horizontal axis of the condition screen may represent the injection quantity, the injection condition may be made up of the injection rate and the injection quantity, and the condition image may have a horizontal width corresponding to the injection quantity and include the injection rate as text data. In this case, the liquid injector may automatically calculate the injection time period from the injection rate and the injection quantity and provide the injection time period as text data in the condition image.

In the above embodiment, when the injection rate exceeds the upper limit rate, the color of the condition image is changed and blinked to output a rate alarm. For example, a guidance message as "Critical rate, check the setting" may be provided as an alarm display in the condition image; and/or a dedicated icon may be provided as an alarm image. In addition, a portion of the condition image equal to or lower than the upper limit rate is colored differently from the portion higher than the upper limit rate to notify the operator that the injection rate exceeds the upper limit rate.

In the above embodiment, the data of the injection condition is registered for each region to be imaged in liquid injector 100 and when the operator selects one of the regions to be imaged, the associated injection condition is read out. However, the operator may enter the injection condition to liquid injector 100 and then select the region to be imaged, and thus liquid injector 100 may automatically correct the data of the injection condition for the region to be imaged.

More specifically, a predetermined coefficient is registered for each region to be imaged of a patient in liquid injector 100, liquid injector 100 reads the data of the coefficient associated with the selected region to be imaged, and the read coefficient is multiplied, thereby allowing liquid injector 100 to increase and/or reduce the injection rate, injection time period, and/or injection quantity. In this case, for example, even when a complicated injection condition is entered to provide a constant image contrast, the complicated injection condition may be easily applied to various regions to be imaged.

In addition, when the operator enters the details of the body of a patient to liquid injector 100, liquid injector 100 may automatically correct the injection condition in accordance with the entered details of the body. More specifically, when the operator enters the weight of a patient to liquid injector 100, liquid injector 100 may increase and/or reduce the injection rate, injection time period, and/or injection quantity in proportion to the entered weight.

In this case, a complicated injection condition entered to provide a constant image contrast can be simply adjusted, and the contrast media can be automatically injected with an appropriate quantity, rate, and time period for each patient.

Since there are a plurality of types of contrast media containing effective components at different concentrations, the data of the concentrations for the respective types of contrast media can be registered in liquid injector 100. In this case, when the operator enters the data of the type of the contrast media to liquid injector 100, liquid injector 100 reads the data of the concentration based on the entered type of the contrast media and increases and/or reduce the injection rate, injection time period, and/or injection quantity in inverse proportion to the read data of the concentration, so that the contrast media of each type can be automatically injected appropriately to the patient.

Naturally, the abovementioned adjustments of the injection conditions based on the region to be imaged, the weight, and the type of the contrast media can be combined. In this case, the injection condition entered by the operator as desired is increased and/or reduced by multiplication by the coefficient of the region to be imaged, increased and/or reduced in proportion to the weight, and/or increased and/or reduced in accordance with the type of the contrast media.

In the above embodiment, MRI apparatus 300 is used as an imaging diagnostic apparatus, and liquid injector 100 injects a contrast media for use therewith into patients. However, a MRI apparatus or a PET apparatus may be used as an imaging diagnostic apparatus, and liquid injector 100 may inject a contrast media for use therewith into patients.

In the above embodiment, CPU 121 operates according to the computer program stored in RAM 123 to logically perform the various functions as the various means of liquid injector 100. However, the above functions may be implemented by pieces of hardware, or some of the functions may be stored as software in RAM 123 and the others implemented by pieces of hardware.

What is claimed is:

1. A contrast media injection system, comprising:
   an injection head having at least one piston drive mechanism, and
   a control unit, having a display screen, connected to the injection head, said control unit comprising;
      screen displaying part for producing a condition screen with its vertical axis representing an injection rate of liquid and its horizontal axis representing an injection time period of the liquid;
      condition entering part for accepting an input action, by an operator, for at least one injection condition including an injection rate of the liquid relative to the injection time period;
      condition storing part for storing the entered injection condition;
      image producing part for producing a condition-image icon having a horizontal width corresponding to the injection time period, wherein the icon has a first end and a second end;
      image displaying part for displaying the condition-image icon in the condition screen on the display screen, at a vertical position in association with the injection rate and at a horizontal position in association with the injection time period; and
      wherein the condition entering part is configured to accept (i) an input action for moving the icon upward or downward to thereby change the injection rate, or to accept (ii) an input action for increasing or decreasing the horizontal width of the icon thereby increasing or decreasing the injection time period.

2. A contrast media injection system of claim 1 wherein the condition entering part further accepts an input action of a plurality of the injection conditions for one injection performing mechanism.

3. A contrast media injection system of claim 1 wherein the injection head comprising;
   a first piston drive mechanism for contrast media injection, and
   a second piston drive mechanism for saline injection.

4. A contrast media injection system of claim 3 wherein said image displaying part further displays the condition-image icon for each of the liquids in a different color in the condition screen.

5. A contrast media injection system of claim 1 wherein said control unit further comprising ;
   rate storing part for storing an upper limit rate of the liquid injection in advance; and
   alarm outputting part for outputting an alarm when the injection rate of the stored injection condition exceeds the upper limit rate.

6. A contrast media injection system of claim 1 wherein said control unit further comprising quantity calculating part for calculating an injection quantity of the liquid for each of the injection conditions;
   said image displaying part further displays the condition-image icon together with text data of the quantity of the liquid.

7. A contrast media injection system of claim 1 wherein said screen displaying part further displays the condition-image icon together with text data of the injection rate,
   the control unit further comprising review entering part for accepting an input action of a review instruction,
   the image displaying part enlarges the text data of the condition-image icon when a review instruction is entered.

8. A contrast media injection system of claim 7 wherein the image producing part produces the text data of the condition-image icon as a combination of a numerical value and its unit, and
   the image displaying part enlarges only the text data of the numerical value when the review instruction is entered.

9. A contrast media injection system of claim 8 wherein the image displaying part further displays the text data of the unit outside the condition-image icon when the review instruction is entered.

10. A contrast media injection system of claim 1 wherein the display screen is touch-screen type display.

11. A contrast media injection system of claim 1 wherein the first end of the icon corresponds to a start of the injection time period and the second end of the icon corresponds to an end of the injection time period.

* * * * *

UNITED STATES PATENT AND TRADEMARK OFFICE
CERTIFICATE OF CORRECTION

PATENT NO. : 8,437,835 B2  
APPLICATION NO. : 10/565085  
DATED : May 7, 2013  
INVENTOR(S) : Nemoto Page 1 of 1

It is certified that error appears in the above-identified patent and that said Letters Patent is hereby corrected as shown below:

In the Specification

In column 1 at line 21, Change "ultrasonograph." to --ultrasonography.--.

In column 3 at line 36, Change "is." to --is--.

In column 7 at line 33, Change "defines." to --defines--.

In column 13 at line 10, Change "S35)" to --S35).--.

In column 15 at line 10, Change "timings," to --timings.--.

Signed and Sealed this  
Twenty-ninth Day of October, 2013

Teresa Stanek Rea  
*Deputy Director of the United States Patent and Trademark Office*

UNITED STATES PATENT AND TRADEMARK OFFICE
CERTIFICATE OF CORRECTION

PATENT NO. : 8,437,835 B2  
APPLICATION NO. : 10/565085  
DATED : May 7, 2013  
INVENTOR(S) : Nemoto Page 1 of 1

It is certified that error appears in the above-identified patent and that said Letters Patent is hereby corrected as shown below:

On the title page item (87) PCT Pub. No., Change "WO2005/007200." to --WO2005/007220--.

Signed and Sealed this  
Tenth Day of December, 2013

Margaret A. Focarino  
*Commissioner for Patents of the United States Patent and Trademark Office*